United States Patent
Kotek et al.

(10) Patent No.: US 11,933,869 B2
(45) Date of Patent: Mar. 19, 2024

(54) MAGNETIC RESONANCE IMAGING BASED ON TRANSIENT RESPONSE SIGNALS

(71) Applicant: Erasmus University Medical Center Rotterdam, Rotterdam (NL)

(72) Inventors: Gyula Kotek, Dordrecht (NL); Juan Antonio Hernández Tamames, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 518 days.

(21) Appl. No.: 17/271,726

(22) PCT Filed: Aug. 28, 2019

(86) PCT No.: PCT/NL2019/050551
§ 371 (c)(1),
(2) Date: Feb. 26, 2021

(87) PCT Pub. No.: WO2020/046120
PCT Pub. Date: Mar. 5, 2020

(65) Prior Publication Data
US 2021/0318403 A1 Oct. 14, 2021

(30) Foreign Application Priority Data
Aug. 29, 2018 (EP) .................................. 18191501

(51) Int. Cl.
*G01R 33/50* (2006.01)
*A61B 5/055* (2006.01)
(Continued)

(52) U.S. Cl.
CPC .............. *G01R 33/50* (2013.01); *A61B 5/055* (2013.01); *G01R 33/5608* (2013.01); *G01R 33/5613* (2013.01); *G01R 33/543* (2013.01)

(58) Field of Classification Search
CPC .. G01R 33/50; G01R 33/543; G01R 33/5608; G01R 33/5613
See application file for complete search history.

(56) References Cited

U.S. PATENT DOCUMENTS 7,116,105 B1  10/2006 Zhang
8,723,518 B2   5/2014 Seiberlich et al.
(Continued)

FOREIGN PATENT DOCUMENTS

JP  2000070239 A  3/2000

OTHER PUBLICATIONS

Hargreaves et al., "Characterization and Reduction of the Transient Response in Steady-State MR Imaging", Magnetic Resonance in Medicine, vol. 46, pp. 149-158; 2001.
(Continued)

*Primary Examiner* — Gregory H Curran
(74) *Attorney, Agent, or Firm* — Hoffmann & Baron, LLP

(57) ABSTRACT

A method for magnetic resonance imaging (MRI) comprises applying a consecutive series of MRI sequences to a target volume (V) according to experimental settings (TR, α, β). A discrete sequence of transient response signals (Sn, Sn+1, Sn+2) is measured and fitted to a fit function (F) that is continuously dependent on a sequence number (n) of the respective MRI sequence (Pn) and corresponding response signal (Sn). A shape of the fit function is determined according to an analytically modelled evolution by the experimental parameters (TR, α, β) as well as variable intrinsic parameters (r, λ3, φ, δ) to be fitted. For example, the model is based on an equivalent harmonic oscillator. The intrinsic parameters of the fit function can be related to the intrinsic properties (PD, T1, T2) of the spin systems and used for imaging the target volume (V). Various optimiza-
(Continued)

tions of contrast can be achieved by tuning the experimental settings according to the model.

16 Claims, 10 Drawing Sheets

(51) Int. Cl.
*G01R 33/54* (2006.01)
*G01R 33/56* (2006.01)
*G01R 33/561* (2006.01)

(56) References Cited

U.S. PATENT DOCUMENTS

| | | | |
|---|---|---|---|
| 9,052,372 B2 * | 6/2015 | Palma | G01R 33/50 |
| 10,725,132 B2 * | 7/2020 | Cloos | G01R 33/5608 |
| 2015/0177350 A1 * | 6/2015 | Warntjes | G01R 33/50 |
| | | | 324/309 |

OTHER PUBLICATIONS

Warntjes et al., "Novel Method for Rapid, Simultaneous T1, T2, and Proton Density Quantification", Magnetic Resonance in Medicine, vol. 57, pp. 528-537; 2007.

Rahmer et al., "Merging UTE Imaging, Water-Fat Separation, and T2 Mapping in a Single 3d MSK Scan", Proc. Intl. Socl. Mag. Reson. Med., vol. 18, p. 3224; 2010.

Klaus Scheffler, "On the Transient Phase of Balanced SSFP Sequences", Magnetic Resonance in Medicine, vol. 49, No. 4, pp. 781-783; 2003.

\* cited by examiner

Fig. 14A $$M(t) = \begin{pmatrix} -TR/T_2 & \gamma B_0 - \omega & 0 \\ -(\gamma B_0 - \omega) & -TR/T_2 & \gamma B_1 \\ 0 & -\gamma B_1 & -TR/T_1 \end{pmatrix} \begin{pmatrix} \cos\varphi & 0 & -\sin\varphi \\ 0 & 1 & 0 \\ \sin\varphi & 0 & \cos\varphi \end{pmatrix} M(t) + \begin{pmatrix} 0 \\ 0 \\ M_0/T_1 \end{pmatrix}$$

$$\phantom{M(t) = }\underbrace{\phantom{XXXXXXXXXXXXXXXXXXXXXXX}}_{A(t)} \quad \underbrace{\phantom{XXXXXXXXXXXXXXX}}_{R(t)} \quad \underbrace{\phantom{XXX}}_{U_0}$$

Fig. 14B

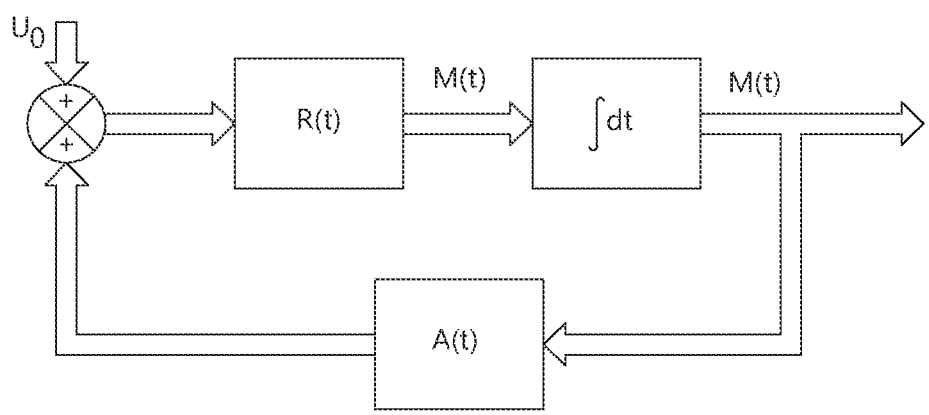

MAGNETIC RESONANCE IMAGING BASED ON TRANSIENT RESPONSE SIGNALS

CROSS-REFERENCE TO RELATED APPLICATIONS

This application is the U.S. National Phase Application of International Application No. PCT/NL2019/050551, filed on Aug. 28, 2019, which claims priority to patent application number EP 18191501.8, filed on Aug. 29, 2018, the disclosures of which are incorporated by reference herein in their entirety.

TECHNICAL FIELD AND BACKGROUND

The present disclosure relates to improvements in the field of Magnetic Resonance Imaging.

Steady-State MRI makes use of a steady state magnetization. Generally, when a sequence of RF excitations and relaxation is repeated with a repetition time (TR) shorter than the T2 relaxation times of the tissue, there may not be enough time for the magnetization to decay completely before the next RF pulse excitation, so that there can be some residual magnetization left over. This residual magnetization is the starting point of the next RF excitation. After a transient phase, where the magnetization still varies between excitations, a steady state may form.

Hargreaves et al. [Magnetic Resonance in Medicine 46:149-158 (2001)] describes characterization and reduction of the transient response in Steady-State MR Imaging, in particular using refocused steady-state free precession (SSFP) sequences. According to Hargreaves, a drawback with such sequences is the slow and often oscillatory signal progression as a steady-state is established and imaging during this transient period can result in image artifacts. Alternatively, waiting for magnetization to reach a steady-state reduces the scan-time efficiency of the imaging method. Hargreaves thus aims to reduce the undesired behavior during the transient phase by generating a two-stage method of "catalyzing," or speeding up the progression to steady-state.

Scheffler [Magnetic Resonance in Medicine 49:781-783 (2003)] describes the transient phase for balanced SSFP sequences. Using the transient magnetization formalism proposed by Hargreaves et al., Scheffler calculates a simulation which shows the signal appears to follow an exponential decay. Scheffler notes there may be small oscillations but believes these are probably negligible. In the discussion and conclusion, Scheffler suggests that the analytical description of the signal recovery can potentially be used to quantify both T1 and T2 relaxation times simultaneously. However, actual implementation is not disclosed.

Seiberlich et al. [U.S. Pat. No. 8,723,518 B2] describes NMR fingerprinting. According to the claimed method at least one member of the series of variable MRI sequences differs from at least one other member of the series of variable MRI sequences. The resulting signal evolutions are acquired and compared to known signal evolutions to characterize the resonant species based on fingerprinting.

Carl Ganter [Magnetic Resonance in Medicine 52:368-375 (2004)] extends the Hargreaves' formalism for off-resonance effects in the transient response of SSFP sequences and obtains approximate solutions for the eigenvalues and eigenvectors only using a first-order perturbation theory.

N. N. Lukzen et al. (Journal of Magnetic Resonance 196 (2009) 164-169) proposes a formalism of generating functions for the analytical expression of signal evolution in periodic trains of sequences. The method does not require the derivation of the expressions for the eigenvalues and the eigenvectors as in the approach of Hargreaves. However, the method may not be generally applicable e.g. for variations in the parameters in the train of sequence blocks.

There remains a need for further improvement such as control and speedup of MRI imaging.

SUMMARY

The present disclosure relates to improvements provided by a method for magnetic resonance imaging, corresponding device, and computer readable medium as defined in the independent claims. Additional advantages may be achieved by embodiments as defined in the dependent claims and/or description that follows.

According to some aspects as described herein, the spin system in MRI is regarded as a linear and dissipative system. For example, in MRI the system may be exposed to repeated MRI sequences (a set of interactions: RF excitation and applied magnetic field gradients), also referred to as probing blocks. It is realized that the immediate response of the system (state of magnetization in the whole object) may in principle contain sufficient information to characterize the system for the purpose of MRI (intrinsic properties such as: PD, T1, T2, T2*, diffusion coefficient etc.). However, it is also realized that this response (echo or free induction decay) may have a relatively short lived nature (~ms), which may not always be sufficient to build a desired image based on the intrinsic properties. To complicate matters, repetition of the probing block before the system has relaxed may typically result in an immediate response of the system that is not identical, even if the parameters of the probing interaction block remains unchanged. And waiting for system equilibration may be too time-consuming.

According to some aspects, the present methods may take advantage of the evolution of the system's response instead of waiting for system equilibration. It is realized that the evolution of the immediate response also carries information of the intrinsic properties. Furthermore it is realized that this evolution can be described mathematically in exact closed form, since the spin system has deterministic and non-chaotic behavior. This provides many advantages. For example, since the evolution of immediate responses can be mathematically described, the train of probing blocks can be designed in an optimal way, so the parameters of interest can be derived by analyzing this evolution.

According to some aspects, the present methods may use unchanged probing parameters between repetitively applied MRI sequences, derive the response evolution for each block, and allow optimization of the probing parameters (RF pulse, gradients, timings). For example, the spin system may exhibit an evolution of responses similar to a damped oscillator. In most cases, this characteristic behavior can have three separate time scales: TR (repetition time: the time between probing blocks, typically on the scale of 10-20 ms), T2 (intrinsic parameter of the spin system, typically on the scale of 50-100 ms) and T1 (intrinsic parameter of the spin system, typically on the scale of 600-1200 ms). The repeated optimal blocks may provide better results than schemes with varying parameters, because the time-scales in the response evolution are maximally separated. Further introduction of a time-scale (e.g. characteristic time of flip angle variation) can link the otherwise separate processes in the system's temporal evolution. The series of immediate responses can be used (e.g. with spatial encoding for single-shot imaging)

to form image series with varying contrast, derived intrinsic parameter maps or detection of deviation from expected behavior due to system imperfections or tissue properties.

As will be explained in further detail below, a mathematical description of the spin ensemble—determined by the intrinsic and secondary parameters and also the measurement parameters—can be described in a formalism that is equivalent to the 3D non-driven damped harmonic oscillator. The description may e.g. rely on the recursive formula on the magnetization vector of the spin ensemble for a repeated block of events (MRI sequence). The recursive formula can be viewed as equivalent to a first order non-homogenous, non-autonomous difference equation. The difference equation can be transformed to a homogenous difference equation with the introduction of a new variable. The first order homogenous difference equation can be transformed to a second order non-autonomous and homogenous equation. This equation can also be extended to the continuous differential equation. The same equation may also describe a non-driven 3D damped harmonic oscillator that is therefore an equivalent damped harmonic oscillator with time-dependent parameter (stiffness or mass) to the magnetization vector of the spin ensemble responding to a repetitive pattern of MRI sequences.

It may be difficult to formulate a general solution for an arbitrary time-dependent term. However there is an exact solution to constant damped harmonic oscillator parameter. The spherical symmetries of a 3D harmonic oscillator yield conserved quantity of angular momentum that allows extension of the constant harmonic oscillator parameter to a variable one and yet result in an exact description to the damped harmonic oscillator and therefore to the spin ensemble and its response to the sequence of blocks. Furthermore, there are special circumstances that are characteristic to medical MR Imaging volumes namely the characteristically different time-scales (TR, T2, T1). The separation of these time-scales allow a uniformly good approximation instead of an exact solution. This method can be used to extend the range of available time-dependent damped harmonic oscillator parameters for optimization of the MRI sequences for targeted signal evolution.

BRIEF DESCRIPTION OF DRAWINGS

These and other features, aspects, and advantages of the apparatus, systems and methods of the present disclosure will become better understood from the following description, appended claims, and accompanying drawing wherein:

FIGS. 14A and 14B illustrates a correspondence between magnetic interactions and an nth-order control system;

DETAILED DESCRIPTION

Figure 1:
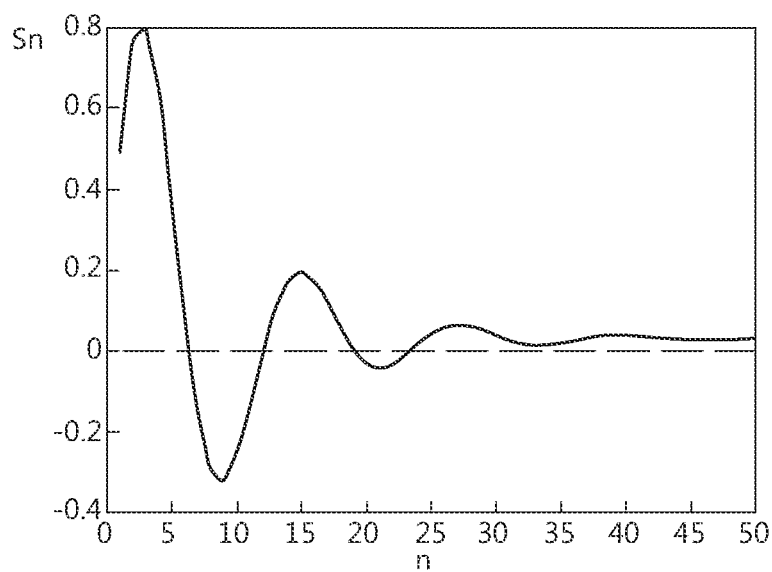
FIGS. 1-11 illustrate various examples in support of the theoretical description.

In the following, we start with a detailed theoretical description which may help in understanding various application for improvement in the field of MR imaging. However it will be understood that practical applications are not bound by details of this theory or the specific examples provided for explaining the various aspects. Instead, this is merely provided to convey a good understanding of the principles, while the scope of applications may include various combinations and/or extensions of these aspects.

Descriptions of MR signals is often based on Bloch equations and the intrinsic properties of $T_1$ and $T_2$ relaxation times. Additionally, or alternatively, we find that the behavior of a spin-system can be described as a 3D harmonic oscillator. Advantageously, such equivalence may allow abandoning the conventional characterization by relaxation times and instead characterize the intrinsic properties by the parameters of e.g. the on-resonance harmonic oscillator model.

In various applications, the evolution of the spin state can be described in a sequence where a series of identical or variable MRI sequences are applied. Instead of attempting to describe the magnetization at any time point, we find it useful to focus on the time points of interest. These time-points of interest are usually at the readout times. Many relevant events can be described in this discrete manner. One advantage found for such description is that the description of the spin state may be treated as a discrete vector problem. For example, this description may be considered equivalent to a vector analysis of a $3^{rd}$ order linear system. It will be appreciated that this approach can allow a simple algebraic description that may be valid for a wide range of MR related applications.

An MRI sequence in a repetitive sequence may typically include one or more of the following elements (not necessarily in this order and not necessarily only one of each per sequence):

an excitation RF pulse which can be generally described as rotation $R_{xy}$ over a flip angle $\alpha$ around an axis in the x-y plane; or more specifically a rotation $R_y$ around the y-axis.

a phase evolution (or precession) which can be described as a rotation $R_z$ over a phase evolution or precession angle $\beta$ around the z axis;

relaxation E which can be transversal in the x-y plane and longitudinal along the z axis.

For example, the elements $R_{xy}$, $R_z$, E can be described as operators acting on a three-dimensional magnetization vector. In the rotating frame of reference the following 3×3 matrices may describe these operators, now taking rotation around the y-axis for the excitation pulse:

$$R_y(\alpha) = \begin{pmatrix} \cos\alpha & 0 & -\sin\alpha \\ 0 & 1 & 0 \\ \sin\alpha & 0 & \cos\alpha \end{pmatrix},$$

$$R_z(\beta) = \begin{pmatrix} \cos\beta & -\sin\beta & 0 \\ \sin\beta & \cos\beta & 0 \\ 0 & 0 & 1 \end{pmatrix},$$

$$E(\tau) = \begin{pmatrix} \varepsilon_2 & 0 & 0 \\ 0 & \varepsilon_2 & 0 \\ 0 & 0 & \varepsilon_1 \end{pmatrix},$$

where $\alpha$ and $\beta$ are the rotation angles. $T_1$ and T2 are the relaxation times, $\tau$ is the duration of relaxation and free precession, $\varepsilon_1 = \exp(-\tau/T_1), \varepsilon_2 = \exp(-\tau/T_2)$.

Typically, it can be assumed that the excitation is a simple rotation around, e.g., the y axis without loosing generality.

It is noted that the operators E and $R_z$ typically commute, i.e.: $[R_z, E]=0$, because they may act independently in subspaces of x-y and z. The operator of the excitation pulse ($R_{xy}$: rotation around an axis in the x-y plane) typically does not commute with these operators. Generally, the events described by E and $R_z$ may not be point-like in time. For example, these processes can be spread out in time and happening simultaneously. Nevertheless operators which are discrete in time can sufficiently describe them in many practical applications.

Operators such as E, $R_y$, and $R_z$ may be sufficient to describe a general MRI sequence. Spoiling for example can be described by an operator like E: e.g. for a perfect spoiling $\varepsilon_1=1$ and $\varepsilon_2=0$. To describe the effect of a gradient: $R_z$ can be used for an effect of phase winding. An operator like E also can describe diffusion. The description of a whole spin ensemble with a distribution of Larmor frequencies is also possible in this formalism. Generally the macroscopic description of the frequency distribution can be included in the relaxation times. In case characteristic ensembles are present then it is also possible to use the algebraic sum of separate magnetization vectors. The operators for the separate magnetization vectors can be chosen to be different.

For the purpose of explaining some of the basic principles applied herein, we start with the case of a repetitive sequence of identical blocks. Later it will be shown that similar teachings may also be applied to cases including where the experimental parameter between MRI sequences are varied.

In one example, let us pick a time-point of interest after the excitation pulse. In the example, let us assume a MRI sequence consisting of excitation, relaxation and phase winding (due to off-resonance or unbalanced gradients). We can assume that before the train of identical MRI sequences the system was in equilibrium with magnetization of $m_0$. We define here $m_0^+$ as the initial magnetization after the excitation pulse, $m_0^+=R_y\, m_0$.

As description of the evolution of the magnetization after the excitation pulse from block to block we can use, for example, the following propagator operator A:

$$A=R_y(\alpha)R_z(\beta)E(T_R), \quad (1)$$

where $\alpha$ is the excitation angle, $\beta$ is the phase evolution during the repetition time $T_R$ (time between the beginning of two consecutive MRI sequences). The evolution of the magnetization can be described in a recursive relation:

$$m_{n+1}^+=A\, m_n^+ + g, \quad (2)$$

where g is the additive vector term of the $T_1$ relaxation: $g=(1-\varepsilon_1)\, m_{eq}$, and $m_{eq}$ is the equilibrium magnetization $m_{eq}=(0,0,m_0)$. From this recursive equation one can derive an expression for $m_n^+$.

This can be done in several ways: with generating function technique or solving the continuous analogue inhomogeneous differential equation. Here we follow the solution to the discrete difference equation after homogenizing the equation (this was previously suggested for the purpose of catalyzing the transient state by Hargreaves et al. [Magnetic Resonance in Medicine 46:149-158 (2001)]). We introduce a new variable $\mu_n=m_n-m_{ss}$. $m_{ss}$ is the magnetization in the steady state that satisfies the next expression:

$$m_{ss}=A\, m_{ss}+g \quad (3)$$

This leads to a homogeneous recursive equation:

$$\mu_{n+1}=A\, \mu_n, \quad (4)$$

with the solution:

$$\mu_n=A^n\mu_0 \quad (5)$$

This vector equation can be simplified with the diagonalization of A. A can be diagonalized with matrix P, of which the columns are the eigenvectors of A. If $\det(P)\neq 0$ then P $AP^{-1}=\Lambda$, where P is the matrix formed from the eigenvectors of A and $\Lambda$ is the diagonal matrix with the eigenvalues of A. The expression for $\mu_n$ can be written in the following form:

$$\mu_n=P\Lambda^n P^{-1}\cdot\mu_0 \quad (6)$$

It will be appreciated that this expression signifies is a linear combination of the $n^{th}$ power of the eigenvalues.

We now turn to some properties of the eigenvalues. The matrix A is a real 3×3 matrix, therefore its eigenvalues $\lambda_1$, $\lambda_2$, and $\lambda_3$ generally satisfy one of the following (in either case A can be diagonalized).

a) Underdamped:
one of the eigenvalues is real ($\lambda_3\in\mathbb{R}$ and the other two are complex conjugates of each other ($\lambda_1=\lambda_2^*$); $\lambda_1=r\cdot e^{i\,\varphi}$, $\lambda_2=r\cdot e^{-i\,\varphi}$.

b) Critical damped:
all eigenvalues are real and of them are identical (degenerate case), c) Overdamped:
all eigenvalues are real and $\lambda_1=r\cdot e^{\varphi}$, $\lambda_2=r\cdot e^{-\varphi}$ The case of triple degeneracy where all the eigenvalues are the same and real can be excluded. Such degeneracy would indicate a spherical symmetry which is normally unrealistic due to the relaxation processes. The spherical symmetry would be possible if $T_1=T_2$, in which case the relaxation matrix is the product of a number and the identity matrix.

It may be noted that there are two different sets of parameters involved in the equations: intrinsic parameters of the system under investigation (e.g.: T1, T2), and experimental parameters which can be influenced (e.g.: TR, $\alpha$, $\beta$). Depending on the actual values of these two sets of parameters, different characteristic eigenvalues can appear. So, depending e.g. on selection of experimental parameters in relation to (expected) intrinsic parameters, the resulting signal may exhibit different behaviors: underdamped (2 complex eigenvalues and 1 real), critically damped (all the eigenvalues are real and 2 of them are identical), overdamped (all of them are real and different). In the underdamped case there is an oscillation with exponentially decreasing amplitude. In the critical damping a single exponential decay is present. In the overdamped case a bi-exponential decay occurs (the exponents are not independent). It will be appreciated that oscillation occurring in the underdamped case may provide further opportunity to recover parameters from the measured signal such a frequency, phase, and decay constant, compared e.g. to a bi-exponential or single exponential response.

In case of a general operator or matrix A it may not be evident how the real and complex eigenvalues depend on intrinsic and experimental parameters since the expressions are the roots of a third order polynomial. Neither may it be evident for their linear combination since the eigenvectors (columns of P matrix) are complex. Nevertheless, without relying on further details of matrix A, it is found that the solution in equation (6) typically yields oscillatory and decay terms. Both terms are power of n functions. The absolute values of the eigenvalues are smaller than one. So it can be considered that the magnetization vector $\mu_n$ exhibits behavior similar to a 3D autonomous damped harmonic oscillator.

In an MR experiment the transversal projection (x-y plane) of the magnetization vector is typically detected. A further projection is a 1D projection, where the phase of the sampling of the signal is predetermined ($\delta$). To emphasize the oscillatory and decay behavior it is found that the signal $S_n$ of the nth block can be written in the following form:

$$S_n = a \cdot e^{-|lnr| \cdot n} \cos(\varphi n + \delta) + b \cdot e^{-|ln \lambda_3| \cdot n} + c, \quad (7)$$

where a, b and c are real coefficients, and $\varphi$, r, $\lambda_3$ are related to the description of eigenvalues as discussed earlier.

Generally, at equilibrium, spins of a system may precess around the main magnetic field or B0-field (e.g. z-axis). The precession typically occurs at the respective Larmor frequency which depends on the experimental condition of the magnetic field and the gyromagnetic ratio which is intrinsic to the precessing system. In an example where a flip angle rotation pulse of 90-degrees is applied, this may cause the spins to precess in the x-y plane, creating observable magnetization. Typically, the rotation pulse is actually another, weaker magnetic field (B1) that oscillates very rapidly. If the frequency of this oscillating magnetic field is at, or close enough to the Larmor frequency of the spins in the sample, it is said to fulfill the resonance condition ("on-resonance"), and in effect may tilt the spins e.g. 90-degrees to the x-y plane. If the frequency of the B1-field is far from the Larmor frequency ("off-resonance"), the spin may not tilt all the way to x-y plane. This might lead to a different, e.g. weaker, signal. Off-resonance cases may occur deliberately or e.g. where the B0-field is not exactly known or controlled.

For simplicity, we now turn to applications where the propagator operator can be written in the form:

$$A = R_y \cdot E$$

For example, this may correspond to an on-resonance case, but may also refer e.g. to a balanced gradient case (zero moment of the gradients is null in $T_R$). Later we will also discuss other, e.g. off-resonance, cases.

The sequence in the on-resonance case can be considered as a two-dimensional problem, e.g. where the 1D subspace (defined by the excitation axis) and the other 2D subspaces can be considered disjunct. The behavior of the system in the 1D subspace is a trivial $T_2$ decay. In this case, the eigenvalues can be calculated as the roots of a $2^{nd}$ order polynomial. So the eigenvalues of A may take the form:

$$\lambda_{1,2} = \tfrac{1}{2}[(\varepsilon_1 + \varepsilon_2) \cos \alpha \pm \sqrt{-4\varepsilon_1\varepsilon_2 + (\varepsilon_1+\varepsilon_2)^2 \cdot \cos^2 \alpha}] \lambda_3 = \varepsilon_2$$

In the underdamped case, the parameters of oscillation and decay in equation (7) can be written as:

$$r = \sqrt{\varepsilon_1 \varepsilon_2}$$

$$\phi = \arctan\left(\sqrt{\frac{4\varepsilon_1\varepsilon_2}{(\varepsilon_1+\varepsilon_2)^2 \cos^2\alpha} - 1}\right)$$

$$\delta = 0,$$

assuming that the phase of the detection and the excitation pulse are the same.

In the overdamped case $\varphi$ is purely imaginary:

$$\phi = i \cdot \arctan\left(\sqrt{\frac{4\varepsilon_1\varepsilon_2}{(\varepsilon_1+\varepsilon_2)^2 \cos^2\alpha} - 1}\right),$$

and equation (7) can be written as:

$$S_n = a \cdot e^{-|lnr| \cdot n} \cos(\varphi n + \delta) + b \cdot e^{-|ln \lambda_3| \cdot n} + c, \quad (8)$$

where r and $\lambda_3$ are real and smaller than 1.

The critical value of the excitation flip angle can be written as:

$$\alpha_c = \arccos\left(\sqrt{\frac{4\varepsilon_1\varepsilon_2}{(\varepsilon_1+\varepsilon_2)^2}}\right),$$

where in the argument appears the ratio of the geometrical and the arithmetic means of $\varepsilon_1$ and $\varepsilon_2$. The argument of the arcus cosine function is between zero and one, i.e. it is the square of the ratio of the geometrical and the arithmetic means of $\varepsilon_1$ and $\varepsilon_2$. Consequently $\alpha_c$ exists and is in the interval of $[0, \pi/2]$.

Below this excitation angle the system is overdamped and exhibits purely decaying behavior. At the critical flip angle the system exhibits no oscillation and an exponential decay. The signal decay is mono-exponential if the phase of the signal detection and the excitation RF pulse are the same. Above this value the system is underdamped with an oscillation frequency of $\varphi/2\pi$ and an exponential decay with n.

FIG. 1 shows an example of evolution of the signal Sn as a function of block number n using intrinsic system parameters: T1=800 ms, T2=50 ms, and experimental parameters: repetition time TR=12 ms, flip angle $\alpha$=30 degrees, on-resonance case. The signal may be considered as a 1D projection of the 3D harmonic oscillation in the on-resonance, under-damped case.

The signal has the following characteristics. The decay exponent is an intrinsic system parameter: $\ln(\sqrt{\varepsilon_1\varepsilon_2})$. The phase is trivial and carries no information about the system. The frequency also is trivial in the high flip angle range, but carries information about the intrinsic properties of the system closer to the critical angle. The steady state value is an important intrinsic parameter, however it also depends on the flip angle.

Figure 2:
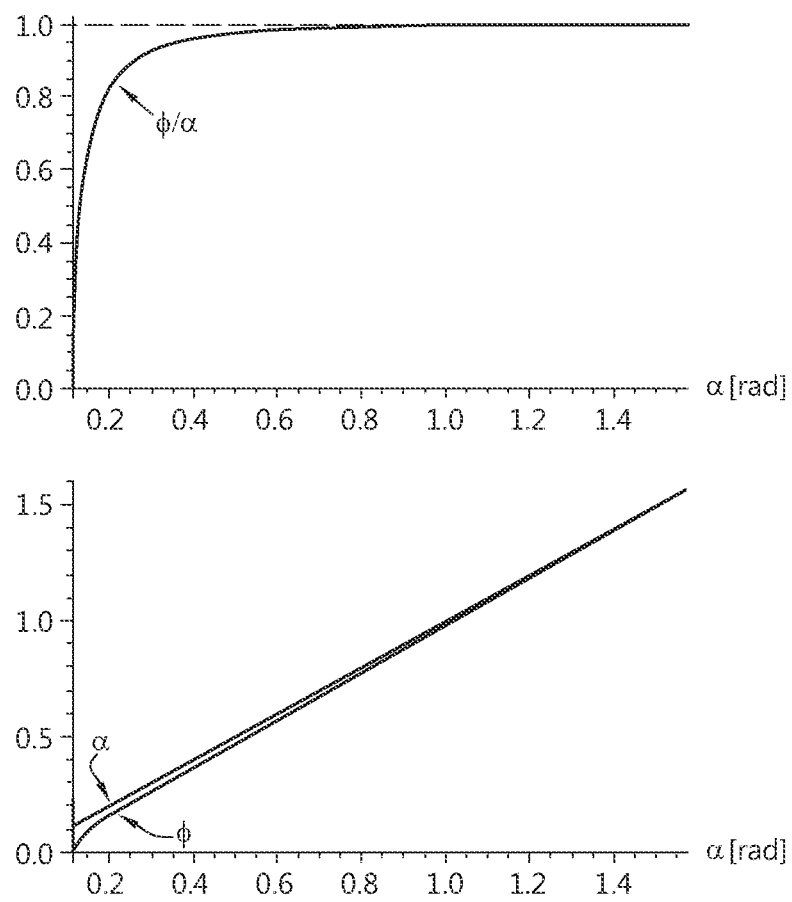

FIG. 2 shows a comparison between the experimental flip angle $\alpha$ and resulting oscillation frequency $\varphi$ (angular velocity) of the signal Sn. The other parameters are the same as FIG. 1, i.e. T1=800 ms, T2=50 ms, TR=12 ms. It will be noted that the oscillation frequency is typically close to $\alpha/2\pi$ at higher flip angles $\alpha$, although not quite equal. The difference may be more pronounced when the time-scales $T_2$ and $T_R$ are not well separated.

The signal detection in MR can be phase sensitive, the phase can be chosen arbitrarily also after acquisition and image reconstruction. When quadrature signal is registered, the phase is fixed and we can speak of real and imaginary signal and images. In the context of our discussion the phase we refer to is the phase of the real signal and image. The phase of the RF excitation pulse and the real channel are identical. The phase of the on-resonance signal acquired by the repetitive sequence pattern is zero.

The steady state can be written as:

$$m_{ss} = (I - R_y(\alpha) \cdot E(T_R, T_1, T_2))^{-1} \cdot m_0$$

So this may depend not only on intrinsic parameters, but also on the experimental parameters of the excitation flip angle $\alpha$ and repetition time TR. These experimental parameters can be well controlled in a known way and/or independently measured.

In the phase corrected detection there is only one observable exponent (see equation (7)):

$$-|ln(r)| = \ln \sqrt{\varepsilon_1\varepsilon_2}$$

This exponent depends exclusively on intrinsic parameters $T_1$ and T2.

The on-resonance sequence exhibits a critical damping behavior at the critical flip angle. The exponent of the mono-exponential decay is: $\ln \sqrt{\varepsilon_1\varepsilon_1}$.

Figure 3:
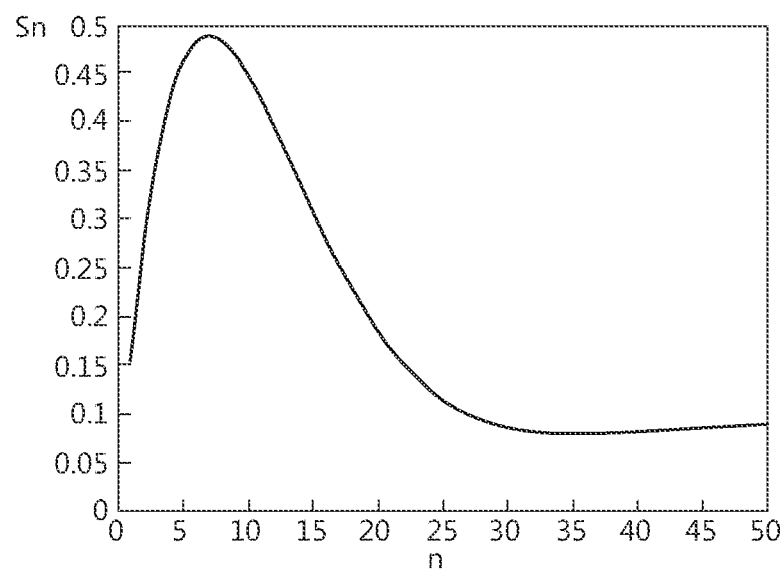

FIG. 3 shows signal evolution again for the case T1=800 ms, T2=50 ms, TR=12 ms, but now with flip angle α=9.087 degrees. This illustrates an example of on-resonance, critical damping.

Figure 4:
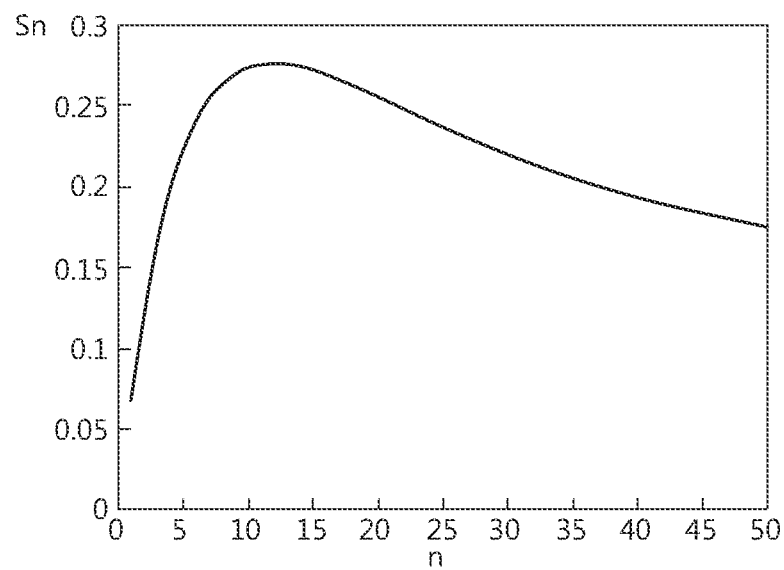

FIG. 4 shows signal evolution again for the case T1=800 ms, T2=50 ms, TR=12 ms, but now with flip angle α=4 degrees. This illustrates and example of the overdamped case. In the overdamped case (excitation flip angle is below the critical value) we can observe a cosine hyperbolic decay in the phase correct measurement (see equation (8)). The information content of the exponents is the same as in the underdamped case.

Figure 5:
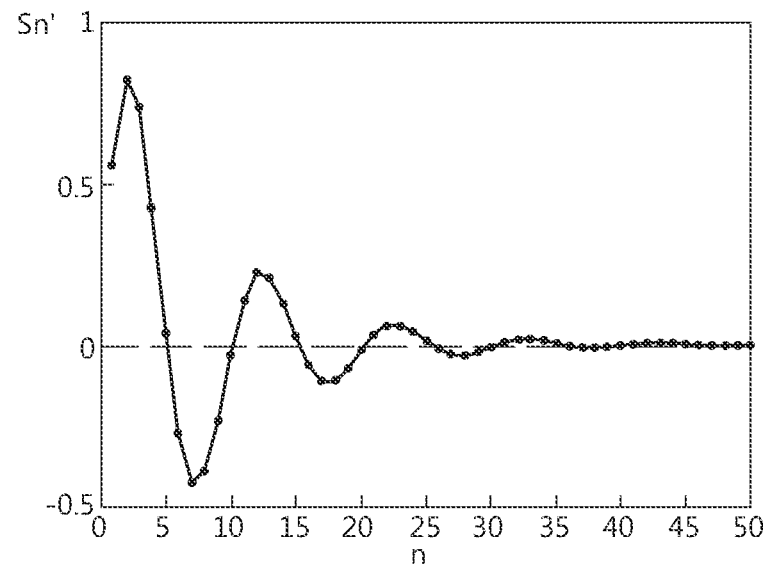

FIG. 5 shows a simulated on-resonance signal and the fitted theoretical model. Circles indicate the simulated signal Sn', with steady state removed and phased. Connected stars indicate a fit with the theoretical model. The estimated (l1 norm fitting) frequency and the exponential decay is found to be within 0.5% and 2% error of the true values, in this case T1=800 ms, T2=50 ms, TR=12 ms, and flip angle α=36 degrees Based on the present findings, it may be realized that the on-resonance case can be essentially treated as a 2D problem. The signal detection is a further projection to one dimension. The general one-dimensional harmonic oscillator exhibits the same properties: overdamped, critical and underdamped.

The general equation for an autonomous 1D harmonic oscillator can be written as:

$$\frac{d^2x}{dt^2} + 2\zeta\omega_0 \frac{dx}{dt} + \omega_0^2 x = 0$$

where x is the time dependent coordinate of the oscillator, $\omega_0$ is the undamped angular frequency of the oscillator, and $\zeta$ is the damping ratio, where in this case critical damping occurs at $\zeta=1$.

It may not be trivial that the 2D oscillator exhibits critical behavior. Critical damping occurs when the propagator operator has degenerate eigenvalues in the disjunct 2D subspace (perpendicular plane to the axis of excitation, in our discussion the x-z plane). The degeneracy may imply the existence of symmetry in the system. The existence of such symmetry may not be trivial. Such degeneracy can e.g. be connected to a preserved quantity. In general, the Bloch equation—due to the dissipative terms of $T_1$ and $T_2$ relaxation—does not indicate obvious preserved quantities. For our immediate purposes it is not essential to find the symmetry and their preserved quantities. It is worthwhile to mention here that this degeneracy as we will see—may not be present in the general off-resonance case.

We will now turn to the general off-resonance case. For our purposes we refer to "off-resonance" when the propagator takes the following form:

$A = R_y \cdot R_z \cdot E$, where $R_y = R_y(\alpha)$ is the excitation as a rotation operator with flip angle α and $R_z = R_z(\beta)$ is describing phase evolution β during $T_R$ as a rotation around the z axis. The phase evolution can be caused e.g. by unbalanced gradients or simple off-resonance.

In this case too, the evolution of the magnetization can adequately be described by equation (6). The eigenvalues of A are the roots of a third order polynomial. Unlike in the on-resonance case, there are no disjunct sub-spaces. Therefore, there is no trivial eigenvalue (like $\varepsilon_2$ in the disjunct 1D space). The eigenvalues have the properties as described above. A major difference from the on-resonance case is that the eigenvalues may depend not only on the intrinsic but also on the experimental parameters which can be used to advantage in some cases.

Figure 6:
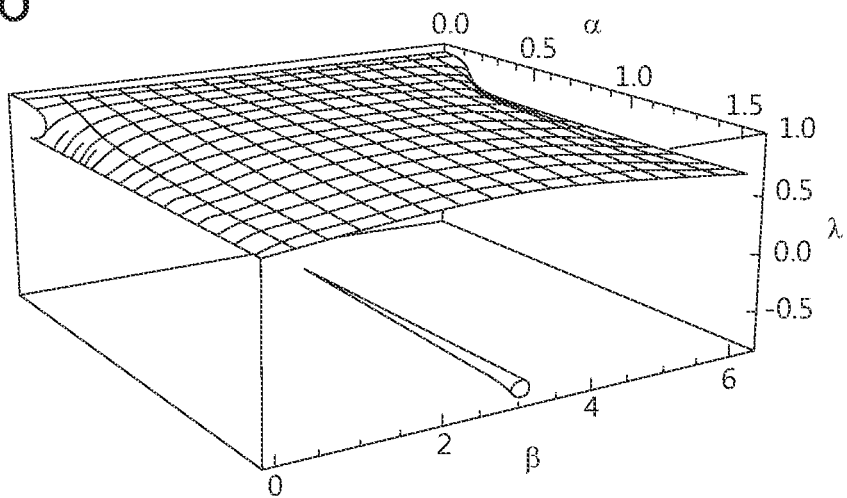

FIG. 6 depicts the eigenvalues λ (plotted only when real) as functions of excitation flip angle α and phase evolution angle β. Intrinsic values used here: T1=800 ms, T2=30 ms; with the experimental parameter of the repetition time TR=12 ms. Top plane: always real eigenvalue, Bottom (tube): other two eigenvalues when real.

Figure 7:
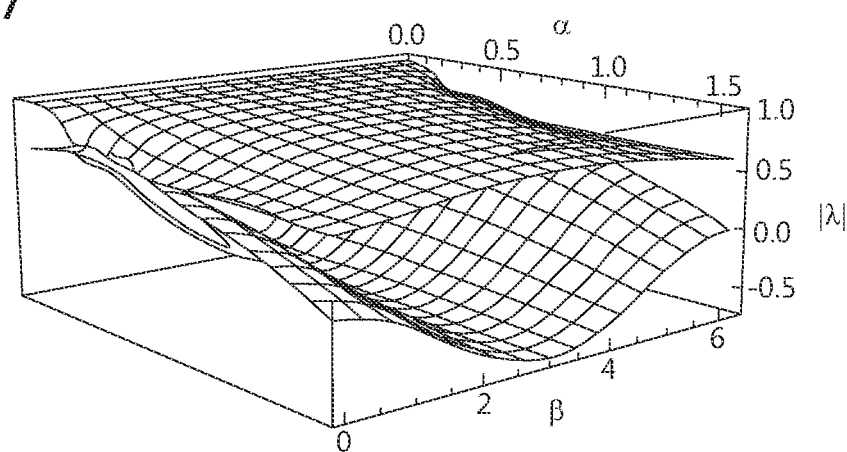
Figure 8:
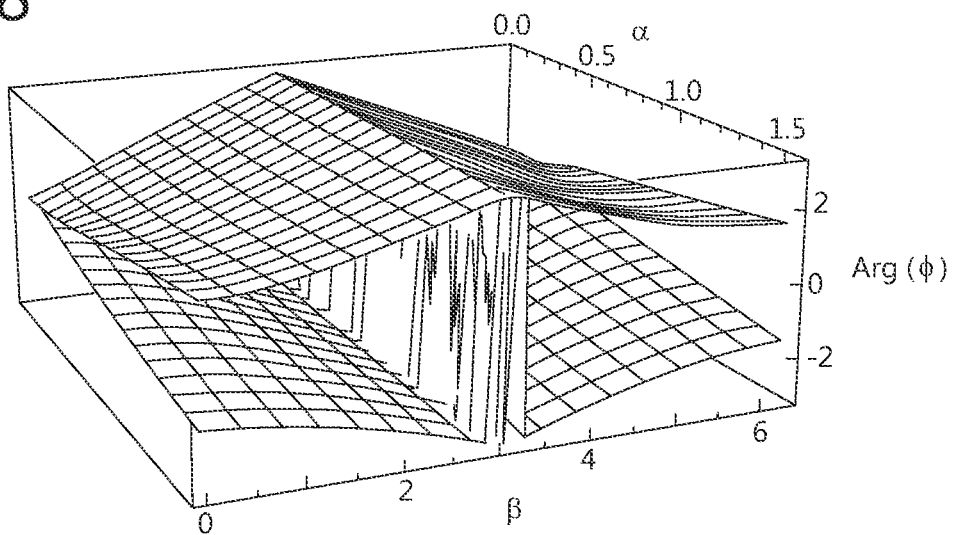

FIG. 7 shows the absolute values of the eigenvalues |λ|. Top plane: always real eigenvalue, Bottom plane: absolute value of the other two eigenvalues FIG. 8 shows the argument (φ) of the two complex eigenvalues. Surfaces: argument of the two other eigenvalues An interesting property of the eigenvalues may be observed when off-resonance is introduced: there is only one real eigenvalue, the other two are complex and are complex conjugate of each other. This may be valid in a wide range of experimental and intrinsic parameters, except for the very near proximity to β=0, π. In this case, the critical behavior does not exist. The degeneracy of the 2D case disappears. A closer inspection of the propagator of the on- and off-resonance cases may provide further insight. For example, the difference of the off- and the on-resonance propagator can be a useful expression to investigate the low/3 values in a perturbation theory approach:

$$\begin{pmatrix} \varepsilon_2 \cos\alpha(-1+\cos\beta) & \varepsilon_2 \cos\alpha \sin\beta & 0 \\ -\varepsilon_2 \sin\beta & \varepsilon_2(-1+\cos\beta) & 0 \\ \varepsilon_2 \sin\alpha(-1+\cos\beta) & -\varepsilon_2 \cos\alpha \sin\beta & 0 \end{pmatrix}$$

The degenerate eigenvalue for the β=0 case is split and are shifted towards 0 and the other one towards $\varepsilon_1$. The eigenvalues are bound to be in the interval [0,1]. With increasing/β the shift reaches the boundaries very quickly.

The symmetry and preserved quantity hidden in the on-resonant case disappears very quickly with the introduction of off-resonance. As a notable consequence: the off-resonance case does not exhibit the critical damping behavior, there is always oscillation present in the signal. This will be very useful in short T2 species, where even at lower flip angles it is possible to induce oscillation. Below are the figures that depict the signal evolution with the same parameters as in the previous on-resonance figures. The difference is that a phase evolution is introduced. This phase evolution represents the effect of the off-resonance or the unbalanced gradients.

Figure 9:
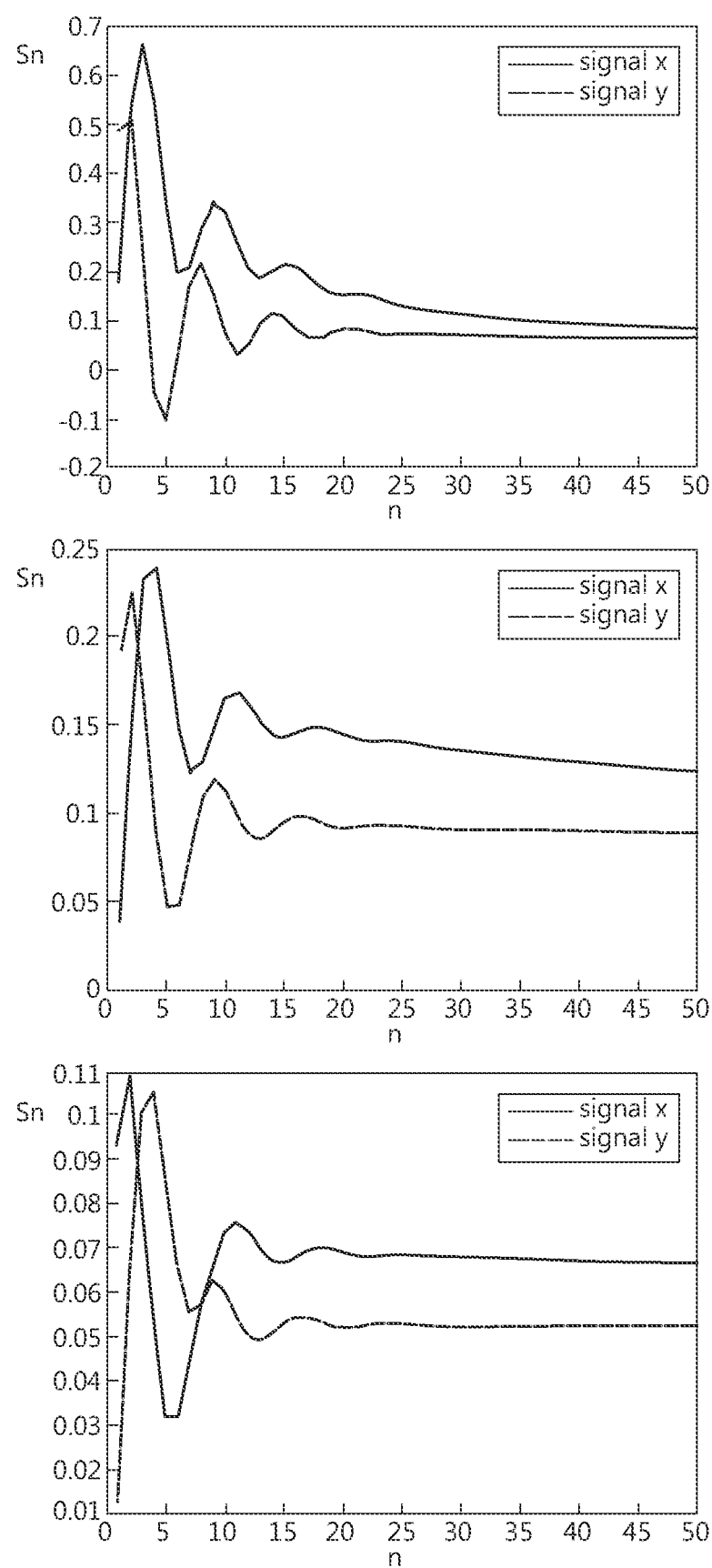

FIG. 9 uses the same parameters as in FIGS. 1,3,4 from top to bottom, with off-resonance. In contrast to the on-resonance case, all three flip angles result in an oscillatory signal.

For easier inspection the signals are phased, i.e. correction applied for the phase difference between excitation and read-out caused by the off-resonance. It is clearly demonstrated here that even for the lowest excitation flip angle the oscillation is maintained.

It is possible to express the evolution of the magnetization (or rather the difference between the magnetization and its steady state value $\mu_n$: see eqn. 5) in a closed form with the propagator and its eigenvalues. As a direct consequence of the Cayley-Hamilton theorem on square matrices, $A^n$ can be expressed in the following form:

$$A^n = \rho^n \cdot \sin(n\varphi) \cdot$$
$$\left[\frac{1}{\varrho \cdot \sin\varphi} \cdot A - \frac{\cos\varphi}{\sin\varphi} \cdot I + \left(-\frac{\eta_3}{\varrho} + \cos\varphi\right) \cdot \frac{(A^2 + \varrho^2 I - 2\varrho \cdot \cos\varphi \cdot A)}{\varrho^2 + \eta_3^2 - 2\varrho\eta_3 \cdot \cos\varphi}\right] + \varrho^n \cdot$$
$$\cos(n\varphi) \cdot \left[I - \frac{(A^2 + \varrho^2 J - 2\varrho \cdot \cos\varphi \cdot A)}{\varrho^2 + \eta_3^2 - 2\varrho\eta_3 \cdot \cos\varphi}\right] + \eta_3^n \cdot \left[\frac{(A^2 + \varrho^2 J - 2\varrho \cdot \cos\varphi \cdot A)}{\varrho^2 + \eta_3^2 - 2\varrho\eta_3 \cdot \cos\varphi}\right]$$

where A is the propagator and I is the identity operator, $\varrho \cdot e^{i\varphi}$, $\varrho \cdot e^{-i\varphi}$ and $\eta_3$ are the eigenvalues of A; $\varrho$ and $\eta_3$ are real numbers, $\varphi$ is generally complex but either purely real or imaginary.

Substituting this expression in eqn. 5 results an expression for $\mu_n$. It explicitly describes the 3D damped harmonic oscillator behavior. In this expression dependence on the echo number n appears in the exponential decay and in the oscillation, the matrix expressions are independent of n. This expression provides a direct insight in the oscillatory and the damped decay behavior of the signal along the repeated blocks at readout points. It is valid also for the general off-resonance case. There are two noteworthy advantages of using the expression for the description of the signal evolution along the echo number. 1. It does not rely on the complex valued eigenvectors. 2. The parameters in the expression are directly related to the Bloch parameters.

We will now take a closer look at the relationship between the eigenvalues. As mentioned before, the expressions for the eigenvalues (roots of third order polynomial) can be too large for analytical evaluation.

Furthermore, their dependence on experimental parameters may cause problems if those deviate from their nominal values. $B_1^+$ and $B_0$ inhomogeneities can be common issues in conventional MRI scanners, leading to unknown excitation flip angle ($\alpha$) and off-resonance ($\beta$).

There are several identities that apply in the comparison between the on- and the off-resonance. Let A be the propagator for on-resonance and B for the off-resonance case.

$$A = R_y \cdot E \text{ and } B = R_y \cdot R_z \cdot E$$

Let the eigenvalues of A be:

$$\lambda_1 = r \cdot e^{i\varphi}, \lambda_2 = r \cdot e^{-i\varphi}, \lambda_3$$

where r, $\lambda_3 \in \mathbb{R}$. $\varphi$ can be real (overdamped case) or imaginary (underdamped case) or zero in the critically damped case.

Let the eigenvalues of B be:

$$\eta_1 = \rho \cdot e^{i\gamma}, \eta_2 = \rho \cdot e^{i\gamma}, \eta_3$$

where $\rho, \eta_3 \in \mathbb{R}$ $\gamma$ can be real (overdamped case) or imaginary (underdamped case) or zero in the critically damped case.

We can use the following properties of determinants. The determinant of a matrix is the product of its eigenvectors:

$$\text{Det}(A) = \lambda_1 \cdot \lambda_2 \cdot \lambda_3 = r^2 \lambda_3 \text{ and } \text{Det}(B) = \eta_1 \cdot \eta_2 \cdot \eta_3 = \rho^2 \eta_3$$

The determinant of a product of two matrices is the product of their determinants. Also the determinant of a rotation is one: $\det(R_z) = 1$.

$$\text{Det}(B) = \text{Det}(A) \cdot \text{Det}(R_z) = \text{Det}(A)$$

The first relationship between the eigenvalues:

$$r^2 / \lambda_3 = \rho^2 \eta_3 \quad (9)$$

We can use the following property of the traces of matrices. The trace of a matrix is the sum of its eigenvalues:

$$\text{Tr}(A) = \lambda_1 + \lambda_2 + \lambda_3 = r(e^{i\varphi} + e^{-i\varphi}) + \lambda_3$$

and $$\text{Tr}(B) = \eta_1 + \eta_2 + \eta_3 = \rho(e^{i\gamma} + e^{-i\gamma}) + \eta_3$$

From the matrices of A and B in the rotating frame of reference:

$$\text{Tr}(B) - \text{Tr}(A) = \varepsilon_2(1 + \cos\alpha)(-1 + \cos\gamma)$$

Our second relationship between the eigenvalues:

$$r(e^{i\gamma} + e^{-i\gamma}) + \eta_3 - \rho(e^{i\varphi}\rho + e^{-i\varphi}) - \lambda_3 = \varepsilon_2(1 + \cos\gamma)(-1 + \cos\beta) \quad (10)$$

The third and fourth relationship is derived from combining $R_y(\alpha)$ and $R_z(\beta)$ into a single rotation $R_n(\vartheta)$. Here n denotes the unit length vector defining the axis of the combined rotation, $\vartheta$ is the angle of the combined rotation.

With some calculation (e.g. from rotation representation by 2×2 unitary matrices) the relationship between the angles can be written as follows:

$$\cos\frac{\vartheta}{2} = \cos\frac{\alpha}{2} \cdot \cos\frac{\beta}{2} \quad (11)$$

The rotation angles may be related to the eigenvalues:

$$\varphi = \arctan\left(\sqrt{\frac{4\varepsilon_1\varepsilon_2}{(\varepsilon_1 + \varepsilon_2)^2 \cos^2\alpha} - 1}\right) \quad (12a)$$

$$\gamma = \arctan\left(\sqrt{\frac{4\varepsilon_1\varepsilon_2}{(\varepsilon_1 + \varepsilon_2)^2 \cos^2\theta} - 1}\right) \quad (12b)$$

As depicted in FIG. 2, the arguments of the eigenvalues are very close to the rotation angles away from the critical behavior at higher rotation angles:

$$\cos\frac{\gamma}{2} \approx \cos\frac{\varphi}{2} \cdot \cos\frac{\beta}{2} \quad (13)$$

Equations (11) and (12a,b) or (13) are our third relationship between the eigenvalues of A and B. The phase of the signal as a one dimensional projection carries information about the off-resonance. The phase difference from an on-resonance and an off-resonance signal can be derived from the combination of the rotations. The axis of the combined rotation:

$$n = \left(\sin\frac{\alpha}{2} \cdot \sin\frac{\beta}{2}, \ \sin\frac{\alpha}{2} \cdot \cos\frac{\beta}{2}, \ \cos\frac{\alpha}{2} \cdot \sin\frac{\beta}{2}\right)$$

The phase difference:

$$\delta = \frac{\beta}{2} \quad (14)$$

This relationship does not strictly belong to the relationship of the eigenvalues, but can be useful in relating the signal of the general case to the one of the special case of on-resonance.

We will not review relationships between on- and the off-resonance signals. According to one aspect, we wish to determine the intrinsic parameters of the spin system from the evolution of signal intensities in a series of images produced by applying a train of identical MRI sequences. In the following we propose a possible algorithm to derive the intrinsic parameters.

Prior knowledge of experiment parameters may typically include the excitation flip angle α and the repetition time (TR). For example, the repetition time is a well controlled value in a common MR scanner, with fidelity of microseconds. That is an error of less than 0.03%. The actual flip angle may deviate from the nominal value and the relative error can be as high as 10%.

The observed signal in the general case can be described using equation (7):

$$S_n = \alpha \cdot e^{-\ln r \cdot n} \cos(\varphi n + \delta) + b \cdot e^{-\ln \lambda_3 \cdot n} + c \quad (15)$$

In the overdamped case φ is imaginary (or keeping φ as a real number: the cosine function is replaced by the cosine hyperbolic function). We will refer to φ as frequency in either case (for brevity, although more correctly it is angular velocity).

The signal in the general case (avoiding the very special coincidence of β=v·π, where v is an integer number), may be processed e.g. as follows.

Step 1: Fit equation (15) to the measured signal to determine r, $\lambda_3$, φ, δ (two exponents, one frequency and one phase).

Step 2: Optionally, use φ and δ in equation (14) and equation (13) to derive or confirm α and β experimental parameters. Alternatively, if assumptions for equation (13) do not apply: use equations (12a,b) and (11). Alternatively, or additionally, independent measurements can be taken of α and β. For example, $B_1^+$ and $B_0$ mapping may be common in MR scanners as quality assurance techniques.

Step 3: Use equations (9) and (10) to determine r ($\sqrt{\varepsilon_1 \varepsilon_2}$) and $\lambda_3$ ($\varepsilon_2$), all purely intrinsic parameters.

As a result of these steps every parameter of an ideal on-resonance signal is recovered. The properties of the on-resonant signal may describe the intrinsic properties of the spin system. As a side-result, steps 1 and 2 also yield the actual flip angle and the off-resonance. ($B_0$ and $B_1^+$ maps).

Figure 10:
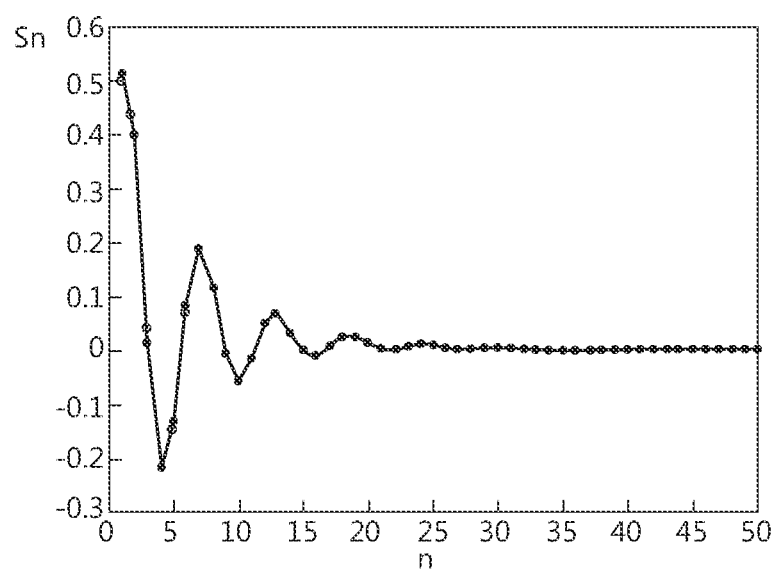

FIG. 10 shows phased signal in the off-resonance case. Circles: signal simulated, with steady state removed and phased. Stars connected: fitted with theoretical model. Parameters derived by fitting are within a few percent off the theoretical values.

It will be appreciated that, given the analytical expressions of the relationship between eigenvalues as noted above, one can determine the relative error of the derived intrinsic parameters inflicted by the error of observables. Equation (9) and (10) in derivation of r lead to a third order polynomial of r. Errors in r have analytical expression as a function of error in observable parameters:

$$Err(r) = Err(p) \cdot \frac{dr}{dp}.$$

So far we focused on the application of a train of identical MRI sequences. Now we discuss a case where the MRI sequences include variable flip angle excitations $\alpha_n$. In this scenario the propagator matrix $A_n$ depends on the MRI sequence number n. Equation (4) and (5) may no longer hold, and the recursive equation can instead be written as:

$$\mu_{n+1} = A_n \mu_n, \quad (16)$$

For example, $A_n$ can be constructed as a product of constant matrices except for the excitation:

$$R_y(\alpha_n) = \begin{pmatrix} \cos \alpha_n & 0 & -\sin \alpha_n \\ 0 & 1 & 0 \\ \sin \alpha_n & 0 & \cos \alpha_n \end{pmatrix},$$

There does not necessarily exist a closed form solution for $\mu_n$ for a general flip angle scheme. Nevertheless, the problem at hand occurs may have precedent in other fields of physics, e.g. quantum physics and astronomy. So various approximation methods may be used to tackle this problem.

One appropriate solution in our case is the multiple scaling methods with non-linear scaling, e.g. see Ramnath et al. [Journal of Mathematical Analysis and Applications 28, 339-364 (1969)]. The method uses the assumption that there exist well-separated time-scales in the problem. This assumption is partly justified for the MR problems. $T_1$ (~1000 ms) and $T_2$ (~50 ms) relaxations are separated by an order of 10 at least. The third time-scale in our problem is $T_R$ (~10 ms). The fourth time-scale is the characteristic time of the variation of the flip angle α. The separation of these from $T_2$ is less than $T_1$ and $T_2$, yet the approximation method may still provide relatively good results.

Our problem can be viewed as a vector equation and thus it may tackled using non-linear scaling. For simplicity, we demonstrate the concept in a geometrical way. Conceptually the method of multiple-time-scales separates the differential equation (equation of motion) into several differential equations. These describe the evolution of the physical parameter of interest on the different time-scales. The lowest order equation (fastest process) results in a solution that is known from the case where no variation is applied. The constants in the equation are then calculated as time dependent parameters from the higher order equation (slower process). In essence the slower processes are modulating the faster processes. To illustrate this we will look into the off-resonance case. For example, we can assume that $T_R$ and the characteristic variation time of a are smaller than the relaxation times.

Figure 11A:
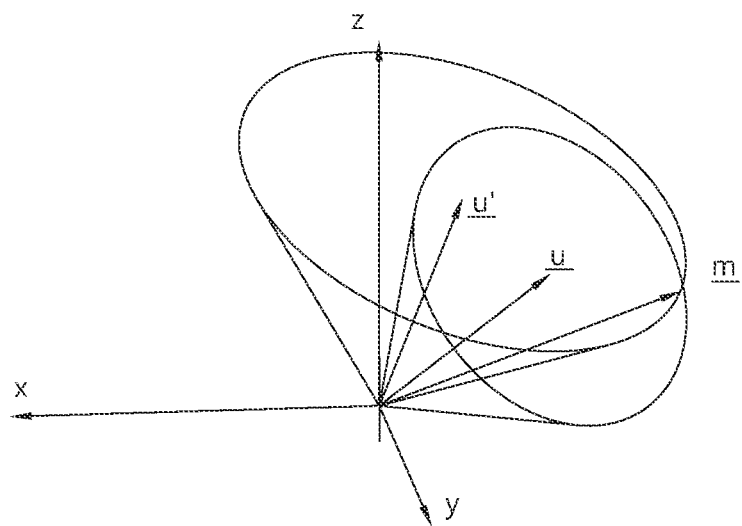
Figure 11B:
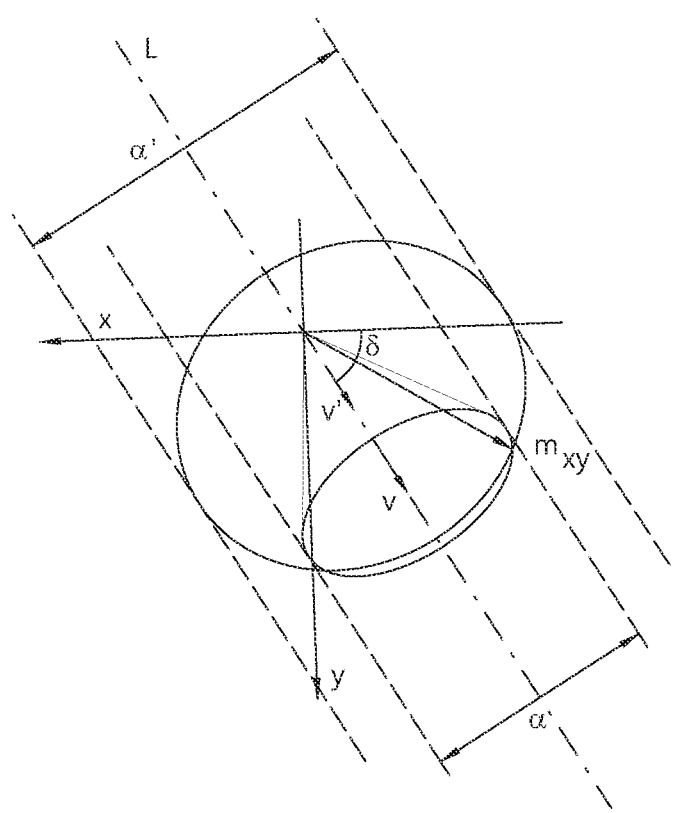

FIG. 11A illustrates the temporal evolution of the magnetization vector m in the rotating frame of reference, when the relaxation times are neglected (fast time-scale). The magnetization vector precesses around in a cone around the vector u (the axis of the combined rotations around y and z: i.e.: excitation and phase evolution due to off-resonance). The trajectory of the tip of vector m is a circle in 3D. The trajectory of the projection of M to the x-y plane (the detection plane) is an ellipse (see FIG. 11b). Its long axis (of length 2α) is perpendicular to the projected line of vector v in the x-y plane having length |v| connecting the center of the ellipse with the origin. The angle between the projected line L and the y-axis is δ.

Eqn. 15 describes the signal behavior for each flip angle as long the flip angle is constant. As the flip angle changes, so do some parameters, but not all of them. For example, δ depends on β only:

$$\delta = \frac{\beta}{2}.$$

δ is the phase difference between the excitation and the readout (see again equation 7.), so is unaffected by variation of the flip angle. Parameter φ depends on the controlled experimental parameters. The "amplitude" parameters a, b and c may depend not only on the actual intrinsic parameters and the experimental parameters, but also on the timing of the flip angle change. However, their new value a', b' and c' can be determined from the knowledge of the actual value of the signal before flip angle change and the flip angles. In the special case of on-resonance the only parameters that are subject to change with flip angle variation are c and φ, the calculation is straightforward So it is demonstrated that since the dependence of the parameters of the signal evolution on α is known, a signal evolution with a known $α_n$ flip angle train can also be described in a closed analytical form.

It is noted that in case of on-resonance there may be critical damping for non-zero flip angle. At the critical flip angle, small variations in sample properties or experimental parameters may cause large differences in signal evolution. When a flip angle scheme sweeps through the critical angle these differences are emphasized. It is generally recommended not to drive a system through unstable states in quantitative experimental setup. Knowing the critical angle and avoiding it in the a scheme is thus recommended. Another safe solution to avoid the critical state may be to introduce off-resonance, i.e. no critical state exists in a wide range of off-resonance phase angles.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise.

Figure 12:
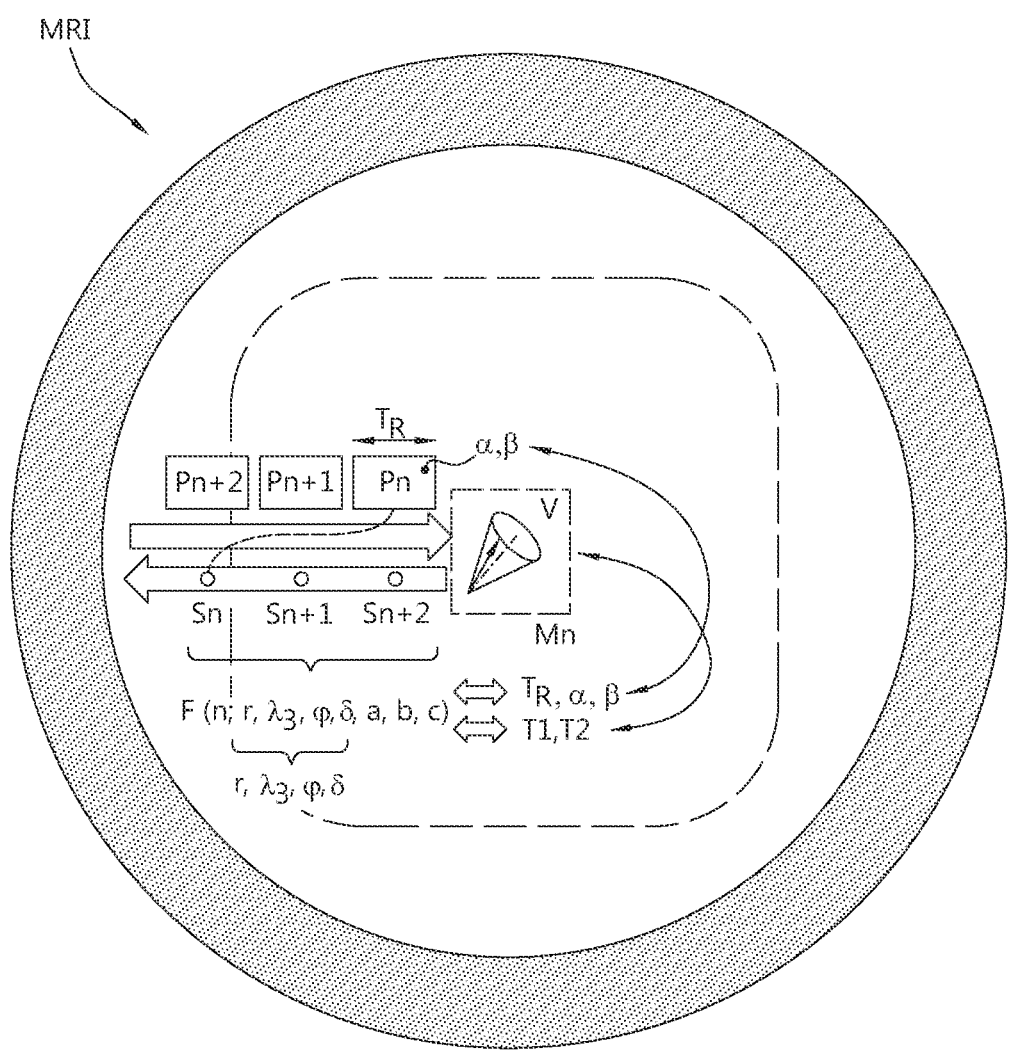
FIGS. 12 and 13 illustrates methods and system for magnetic resonance imaging in accordance with some embodiments.
Figure 13:
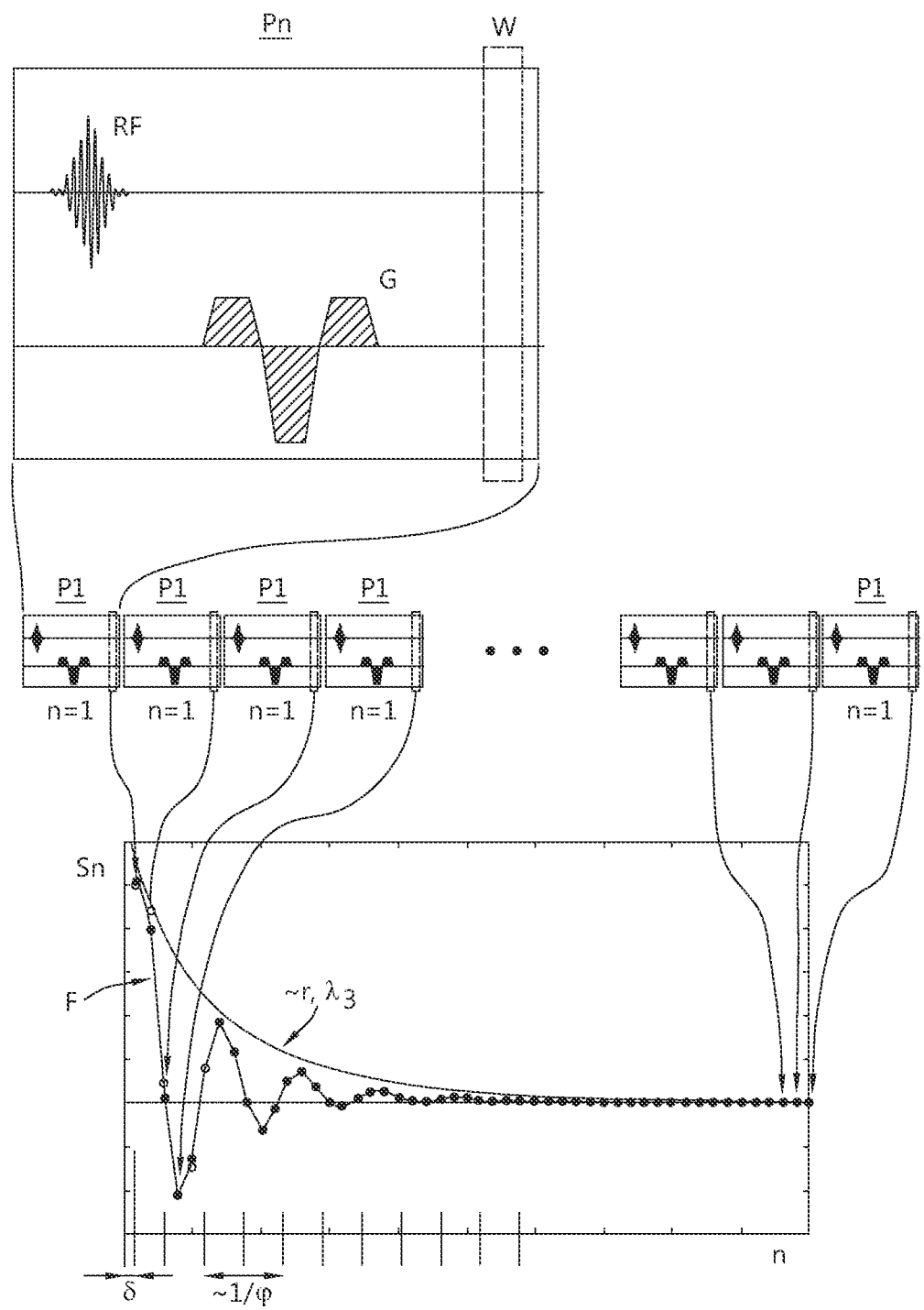

FIGS. 12 and 13 schematically illustrates example features of preferred methods and system for magnetic resonance imaging (MRI).

It will be appreciated that various aspects as described herein can be embodied in practical applications for improving methods and systems related to (nuclear) magnetic resonance imaging such as an MRI device. Some aspects may also be embodied e.g. as a (non-transitory) computer readable medium with software instructions which when executed by an MRI device cause imaging as described herein. While many applications and advantages may already be apparent from the above discussion, we will highlight some of the more preferred aspects in the following. Of course it will be understood that any of these aspects can also be combined with any further teaching having the benefit of the present disclosure.

A preferred embodiment, e.g. as shown in FIG. 12, comprises application of a consecutive series of MRI sequences (here indicated as $P_n$, $P_{n+1}$, $P_{n+2}$) to a target volume "V". For example, the target volume may be a voxel or larger part of a body to be imaged. Typically each MRI sequence $P_n$ comprises an ordered combination of pulses, e.g. radio frequency and/or (magnetic) gradient pulses. The sequence can be configured according to experimental settings for manipulating a magnetization state Mn of spin systems or ensembles to be imaged in the target volume.

With reference again to FIG. 12, a preferred embodiment comprises measuring a (discrete) sequence of transient response signals (here indicated as $S_n$, $S_{n+1}$, $S_{n+2}$). Typically, a respective response signal $S_n$ is acquired during a respective acquisition windows of a respective MRI sequence Sn. For example, an acquisition window W is shown in FIG. 13 (top). In some embodiments, at least one acquisition window is comprised within each MRI sequence. Typically the acquisition window follows the pulse sequence. In FIG. 13 a single acquisition window is shown per sequence, which is preferred. Alternatively, there can be multiple acquisition windows per sequence.

As will be appreciated, the sequence of transient response signals thus measured may represent sequential evolution of the magnetization state Mn resulting from a combination of the manipulating of the spin systems by the MRI sequences as well as intrinsic properties of the spin systems to be imaged.

With reference now to FIG. 13, a preferred embodiment comprises fitting the discrete sequence of transient response signals to a fit function F. As described herein, the fit function F may be continuously dependent on a sequence number (n) of the respective MRI sequence (Pn) and corresponding response signal (Sn). In other words, the fit function may be a continuous function of the variable n associated with the sequence number but defined also for non-integer values of n. For example, as described earlier, the fit function F can be a closed form expression based on an analytically modeled evolution of the magnetization state as a function of the sequence number n. As also described earlier, a shape of the fit function may be determined according to the analytically modelled evolution by the experimental parameters (such as $T_R$, α, β in equation 1) as well as intrinsic parameters (such as r, $λ_3$, φ, δ in equation 7). For example, the intrinsic parameters can be variable and fitted to the measurements.

In FIG. 12 the experimental settings $T_R$, α, β are indicated as examples and in line with the earlier formulas discussed above. However, it will be understood that many other experimental parameters can be set in the MRI sequence to manipulate the magnetization state. Another or further schematic example of an MRI sequence Pn is e.g. shown in in FIG. 13 (top) with a radio frequency pulse RF, and a variable gradient G which has many variable settings such as the timing of the various pulses and acquisition window W. Also in FIG. 12, the intrinsic properties T1,T2 are shown as example but of course the spin system may also have many other intrinsic properties.

For the purpose of imaging, any intrinsic property which may be used to distinguish desired features can in principle be used. Preferably, the intrinsic parameters are at least related or affected by the intrinsic properties of the spin systems to be imaged. In other words, they can be used to characterize these properties or indeed the spin system itself. A preferred embodiment may thus comprise determining an image of the target volume "V" based on one or more fitted values of the variable intrinsic parameters which match the shape of the fit function to the sequence of transient response signals.

In some embodiments, as described herein, the magnetization state is modeled as a three dimensional magnetization vector. For example, the modelled fit function is based on a projection of the magnetization vector in a measurement direction. In a preferred embodiment, the evolution of the magnetization state can be modeled e.g. as the magnetization vector being rotated and/or changing length. In some embodiments, the model may include sequential rotations of the magnetization vector based on the experimental parameters of the MRI sequences and/or intrinsic parameters matching properties of a generic spin system. In other or further embodiments, the model includes decrease of the magnetization vector length based on the experimental parameters and/or intrinsic properties such as relaxation of the spin system.

In one embodiment, as described herein, the effect of an MRI sequence on the magnetization is modeled using matrices as operators on the magnetization vector. For example, the magnetization vector may be multiplied with one or more matrices effecting rotation and/or relaxation of the magnetization vector. Repeated application of fixed or variable MRI sequences can be modelled by repeated multiplication or other operation of the corresponding operators such as matrices on the magnetization vector. Advantageously, the repeated matrix multiplication can in many cases be equated to a closed form expression e.g. using the eigenvalues of the matrix In a preferred embodiment, the evolution of the magnetization state is modeled as a linear dissipative system. For example, the MRI sequences can be viewed as an nth-order control system to generate intrinsic responses equivalent to a linear dissipative system based on intrinsic properties depending on the spin system or species to be imaged. An example of this is illustrated in FIGS. 14A and 14B. For example, FIG. 14A illustrates a pulse sequence atom and FIG. 14B illustrates an equivalent second order control system. In the figures, U0 is the initial magnetization, M(t) the current magnetization, and M(t) with dot the time derivative.

In another or further preferred embodiment, the evolution of the magnetization state is modeled as a harmonic oscillator, more preferably a damped harmonic oscillator, most preferably behaving as an underdamped harmonic oscillator. For example, this may be based on the demonstrated equivalence between application of the Bloch equations to the magnetization vector and the response of a (transient) harmonic oscillator, e.g. to step a function.

In a preferred embodiment, the fit function has both dissipative and oscillatory terms. For example, the modelled fit function may include dissipative terms such as exponentially decaying functions which decrease as a function of their argument which includes the sequence number n. For example, the modelled fit function may includes terms such as sine or cosine functions which oscillate as a function of their argument which includes the sequence number n. Preferably, the modelled fit function includes a product of an oscillatory and dissipative function to represent a physically realistic situation that the oscillation dampens out. It will be appreciated that it may be relatively easy to fit parameters in a function having both dissipative and oscillatory, e.g. compared to a bi-exponential decay.

In one embodiment, the fit function is of a form including terms such as equation 7. For example, the fit function can be like $$F(n) = \alpha \cdot e^{-|\ln r| \cdot n} \cos(\varphi n + \delta) + b \cdot e^{-|\ln \lambda_3| \cdot n} + c,$$

where F(n) is the value of the function to be fitted for the respective measurement of sequence number n; and a, b, c, $\varphi$, $\delta$, r, $\lambda_3$ are fit parameters. Some parameter values, such as the linear factors a, b, and c, may be directly derived or calculated from the response e.g. using linear regression while other parameters may be varied by a fit algorithm. Some values such as "c" may also be derived from the steady state response. Some parameters may also be directly or indirectly determined, or at least estimated, based on experimental settings. Preferably, at least some of the parameters are sufficiently free so they can be used to distinguish spin systems in the measured target volume "V".

For example, the intrinsic parameters may be free parameters in the fit, possibly within predetermined (realistic) bounds depending on the (expected) spin systems to be measured, e.g. depending on a type of tissue or material to be imaged, and/or experimental settings. Of course the fit parameters may also have a degree of covariance either imposed based on physical principles or determined by the fit function. In some embodiments, values for the intrinsic parameters going into the fit may be selected from a limited set of predetermined parameters, e.g. a loop-up table including combinations of parameters previously matched to one or more known tissues or materials. In some embodiments, the parameters corresponding to the experimental settings may be fixed. In other or further embodiments, one or more of the parameters related to the experimental settings may also be adjusted or fitted based on the measurements, e.g. in case they cannot be exactly determined under the measurement conditions such as uncontrolled inhomogeneities.

In a preferred embodiment, the target volume "V" is imaged based directly on the fitted values of one or more of the fit parameters. In other words, it may not be necessary to convert back fitted value of the intrinsic parameters to the conventionally used intrinsic properties such as T1, T2, T2* et cetera. Instead, e.g. the values for one or more of the fitted parameters such as a, b, c, $\varphi$, $\delta$, r, $\lambda_3$ or combinations thereof may be directly used to characterize the measured spin systems in a respective target volume of an MRI image. For example, the magnitude for the fit parameters or combinations of fit parameters can be mapped onto a gray scale to construct an image. Accordingly different gray scale values in the image may correspond to different fitted parameters and can directly be interpreted as corresponding to different tissues. Of course also other variations are possible. For example, using multiple magnitudes, the mapping can also be on a color scale, e.g. using a green value for one parameter, and/or a red value for another parameter, and/or a blue value for a third parameter. Also combinations of hue and brightness can be used to visualize the fitted intrinsic parameters in an MRI image.

In some embodiments, the experimental settings (applied to the MRI device) can be adjusted based on the measured sequence of transient response signals and/or the fitted function. In one embodiment, the experimental settings can be adjusted based on the measured sequence of transient response signals to increase an oscillatory component in the response. For example, an algorithm may change the experimental parameters to increase the fitted factor "a" compared to the fitted factors "b" and/or "c" in the above fit function, which would correspond to a more pronounced oscillatory response.

In a preferred embodiment, the experimental settings are adjusted to increase a contrast in fitted values of an intrinsic parameter between two or more different types of spin systems to be distinguished in the MRI imaging. For example, it was demonstrated that particular combinations of experimental and intrinsic parameters may result in specific types of responses. Accordingly, a set of experimental settings may be selected which provide one type of response for a first set of intrinsic parameters corresponding to a first type of tissue and a second type of response for a second set of intrinsic parameters corresponding to a second type of tissue.

Preferably, first and second types of responses from different tissues are substantially different so they can be well distinguished and used to characterize either type of tissue in the image. For example, the responses may differ in one or more of a different frequency of the (oscillating)

signals, a different amplitude of the signals, a different initial or final offset (steady state) of the signals, a different one or more characteristic time constants of the exponentials (envelope). In some embodiments, the type of signal can be entirely different, e.g. having an oscillating response for one type of tissue and a non-oscillating response for another type of tissue. For example, this may be achieved by setting the experimental settings such that in the one case a threshold for critical damping of the equivalent harmonic oscillator is crossed while in the other case it is not.

Typically, the volume "V" contains a spin ensemble with a distribution of intrinsic properties. For example, the intrinsic properties may include resonance frequencies, T1, T2 and T2* relaxation times, diffusion properties, flow or motion. In some embodiments, an MRI or NMR apparatus is controlled to characterize the spin ensemble based on the equivalence to a damped harmonic oscillator in order to determine: intrinsic properties of the spin ensemble such as PD and T1, T2, T2* relaxation times; spin ensemble secondary characterization such as flow, diffusion, perfusion; measurement specific parameters such as B0 and B1.

Typically, an MRI sequence includes one or more excitation phases, one or more readout phases, and one or more waiting phases. For example, an excitation phase may include the application of radio frequency signals for effecting a flip angle rotation. For example, a waiting phase may include waiting for the magnetization state to evolve, possibly under the influence of a magnetic gradient. For example, a readout phase may include measuring magnetization in an acquisition window, typically following the excitation and waiting phases. Typically, each MRI sequence (Pn) comprises at least a combination of radio frequency (RF) signals and/or magnetic gradients (G) applied to the target volume (V).

Also other or further experimental settings may be used to characterize an MRI sequence, e.g. as described in U.S. Pat. No. 8,723,518 B2, the MRI sequence parameters may comprise one or more of an echo time, flip angle, phase encoding, diffusion encoding, flow encoding, RF pulse amplitude, RF pulse phase, number of RF pulses, type of gradient applied between an excitation portion of a MRI sequence and a readout portion of a MRI sequence, number of gradients applied between an excitation portion of a MRI sequence and a readout portion of a MRI sequence, type of gradient applied between a readout portion of a MRI sequence and an excitation portion of a MRI sequence, number of gradients applied between a readout portion of a MRI sequence and an excitation portion of a sequence block, type of gradient applied during a readout portion of a sequence block, number of gradients applied during a readout portion of a sequence block, amount of RF spoiling, and amount of gradient spoiling.

In some embodiments, each of the MRI sequences is identical. For example, as was demonstrated, a series of identical MRI sequences can be straightforwardly modeled using a closed form expression, e.g. based on the eigenvalues of the matrices used as operators to calculate the effect of the MRI sequence on the magnetization vector. For example, one embodiment comprises the use of a repeated identical MRI sequences and analyzing the transient responses. In another or further embodiment, the repeated identical MRI sequences are adapted to provide an oscillatory response. In a preferred embodiment, the response is fitted to an analytical function based e.g. on an underdamped harmonic oscillator model or equivalent. Most preferably, fit values for the parameters of the analytical function are used directly to construct an MRI image In some embodiments, consecutive MRI sequences may be different by a parametric change of one or more of the experimental settings from one MRI sequence to the next. Parametric changes may be distinguished from random changes, in that the change is controlled by one or more parameters. This means the change is predictable and can still be modelled preferably allowing a closed form expression for a model of the change. At the same time allowing variable MRI sequences may provide further advantage of control over the range of possible responses which can be used to further tune contrast. For example, an experimental setting such as the flip angle may parametrically change by adding or subtracting a fixed value (the parameter) between each consecutive MRI sequence. Also other parameters such as the magnetic gradient may change between sequence block. For example, the magnitude and/or duration of the gradient may change. Also a repetition time or duration of the MRI sequences can be varied. Alternatively, or in addition to varying the MRI sequences, also the timing of acquisition window may change [this can also be seen as an experimental setting].

In one embodiment, an MRI device is calibrated based on a comparison of experimental settings and output experimental parameters according to the fitted function. For example, the fitted values of $\varphi$, $\delta$ (frequency and phase of the oscillations) may be related to the experimentally set flip angle and/or phase evolution $\alpha,\beta$. In some embodiments, a known material or tissue can be placed at the target volume. This may produce a particular response which can be compared to an expected response, e.g. based on a previous measurement or a simultaneous measurement of another volume in the MRI device having the same material. For example, a phantom can be used, for which the relevant intrinsic parameters are known such that discrepancies in the fitting process can be attributed to errors in the actual experimental settings applied compared to the input ones and not in the values for the intrinsic parameters.

In one embodiment, a lookup table or other date structure is provided in a storage, e.g. coupled or accessible to an MRI device. For example, the lookup table may be used for distinguishing different tissues in an image based on a predetermined set of experimental settings and resulting distinct values for one or more of the intrinsic parameters. For example, the experimental settings may comprise an optimized MRI sequence which can optionally also be stored in the lookup table or other storage, e.g. to control the MRI device. For example, the optimized MRI sequence can be fixed or variable between sequences for providing maximum or at least distinguishable contrast in the fitted intrinsic parameters values for imaging between two or more different types of tissue.

Figure 15A:
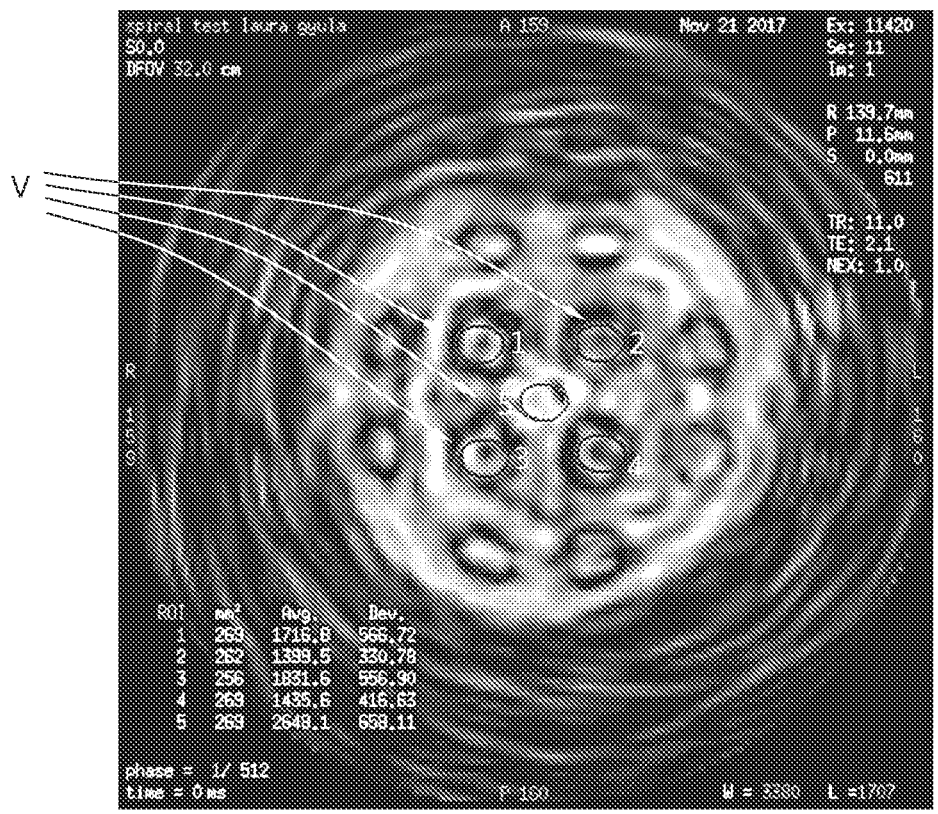
FIGS. 15A and 15B illustrates example measurements.
Figure 15B:
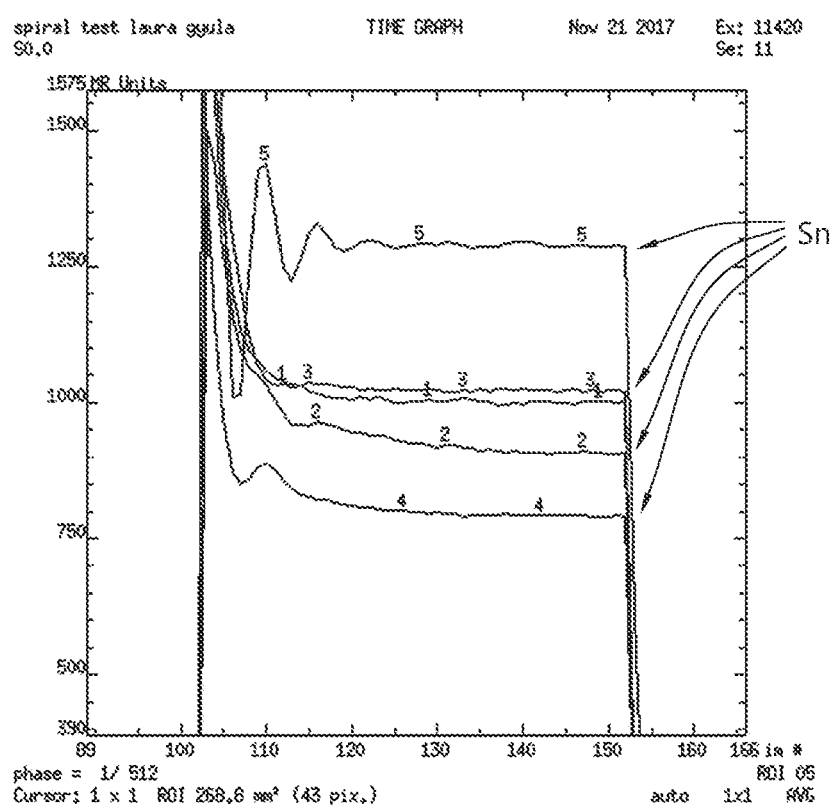

FIG. 15A shows an MRI image of different target volumes "V" and FIG. 15B illustrates the corresponding different response traces Sn.

For the purpose of clarity and a concise description, features are described herein as part of the same or separate embodiments, however, it will be appreciated that the scope of the invention may include embodiments having combinations of all or some of the features described. For example, while embodiments were shown for example pulse sequences, measurements, models, and fit functions, also alternative ways may be envisaged by those skilled in the art having the benefit of the present disclosure for achieving a similar function and result. The various elements of the embodiments as discussed and shown offer certain advantages, such as improvements in magnetic resonance imaging. Of course, it is to be appreciated that any one of the above embodiments or processes may be combined with one or more other embodiments or processes to provide even further improvements in finding and matching designs and advantages. It is appreciated that this disclosure offers particular advantages to MRI or NMR, and in general can be applied for any application for building pulse sequences and/or interpretation of signals.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. A method for magnetic resonance imaging, MRI, the method comprising:
  applying a consecutive series of MRI sequences to a target volume, wherein each MRI sequence comprises an ordered combination of radio frequency excitation pulses and/or magnetic field gradient pulses configured according to experimental settings for manipulating a magnetization state of spin systems to be imaged in the target volume, wherein the MRI sequences are applied during a transient phase with a repetition time between subsequent sequences shorter than a relaxation time of the spin systems to be imaged;
  measuring a discrete sequence of transient response signals, wherein a respective response signal is acquired during a respective acquisition windows of a respective MRI sequence, wherein the sequence of transient response signals represents sequential evolution of the magnetization state resulting from a combination of the manipulating of the spin systems by the MRI sequences as well as intrinsic properties of the spin systems to be imaged, wherein the transient response signals are measured in respective acquisition windows per MRI sequence during the transient phase before a steady state response signal to the consecutive series of MRI sequences develops;
  fitting the discrete sequence of transient response signals to a fit function that is based on an analytically modeled evolution of the magnetization state, wherein the magnetization state is modeled as a three dimensional magnetization vector, wherein an effect of an MRI sequence on the magnetization is modeled using matrices as operators on the magnetization vector, wherein consecutive application of MRI sequences is modelled as repeated multiplication by an operator matrix, wherein the repeated matrix multiplication is calculated using eigenvalues of the operator matrix, wherein the modelled fit function is based on a projection of the magnetization vector in a measurement direction of the measured responses, wherein a shape of the fit function is determined according to the analytically modelled evolution based at least on the experimental settings as well as intrinsic parameters to be fitted, wherein the intrinsic parameters are related to the intrinsic properties of the spin systems to be imaged; and
  determining an image of the target volume based on one or more fitted values of the variable intrinsic parameters which match the shape of the fit function to the discrete sequence of transient response signals.

2. The method according to claim 1, wherein the experimental parameters are selected to result in a fit function with a shape describing the evolution of the magnetization state as a linear dissipative system.

3. The method according to claim 1, wherein the fit function describing the evolution of the magnetization state is shaped as a damped harmonic oscillator model.

4. The method according to claim 1, wherein the fit function has both dissipative and oscillatory terms.

5. The method according to claim 1, wherein the fit function is of the form $$F(n)=a\cdot e^{-|\ln r|\cdot n}\cos(\varphi n+\delta)+b\cdot e^{-|\ln\lambda_3|\cdot n}+c,$$

where F(n) is the value of the function to be fitted for the respective measurement of MRI sequence number n; and a, b, c, $\varphi$, $\delta$, r, $\lambda_3$ are fit parameters.

6. The method according to claim 1, wherein the image of the target volume is based directly on fitted values of one or more fit parameters in the fit function.

7. The method according to claim 1, wherein the method is repeated while the experimental settings are adjusted based on the measured sequence of transient response signals to increase a contrast in fitted values of an intrinsic parameter between two or more different types of spin systems to be distinguished in the MRI imaging.

8. The method according to claim 7, wherein the method is repeated while the experimental settings are adjusted based on the measured sequence of transient response signals to increase an oscillatory component in the response.

9. The method according to claim 1, comprising calibration of an MRI device based on a comparison of experimental settings which are assumed to be inputted to the MRI device, and output parameters according to the fitted function which are related, by the analytic model, to the experimental settings.

10. The method according to claim 1, wherein the fit function is a closed form expression that is continuously dependent on a variable which at integer values equals a sequence number of the respective MRI sequence and corresponding response signal.

11. The method according to claim 1, wherein each of the MRI sequences is identical.

12. The method according to claim 1, wherein consecutive MRI sequences are different by a parametric change of one or more of the experimental settings from one MRI sequence to the next.

13. An MRI device configured to:
  apply a consecutive series of MRI sequences to a target volume, wherein each MRI sequence comprises an ordered combination of radio frequency excitation pulses and/or magnetic field gradient pulses configured according to experimental settings for manipulating a magnetization state of spin systems to be imaged in the target volume, wherein the MRI sequences are applied during a transient phase with a repetition time between subsequent sequences shorter than a relaxation time of the spin systems to be imaged;
  measure a discrete sequence of transient response signals, wherein a respective response signal is acquired during a respective acquisition windows of a respective MRI sequence, wherein the sequence of transient response signals represents sequential evolution of the magnetization state resulting from a combination of the manipulating of the spin systems by the MRI sequences as well as intrinsic properties of the spin systems to be imaged, wherein the transient response signals are measured in respective acquisition windows per MRI sequence during the transient phase before a steady state response signal to the consecutive series of MRI sequences develops;

fit the discrete sequence of transient response signals to a fit function that is based on an analytically modeled evolution of the magnetization state, wherein a shape of the fit function is determined according to the analytically modelled evolution based at least on the experimental settings as well as intrinsic parameters to be fitted, wherein the intrinsic parameters are related to the intrinsic properties of the spin systems to be imaged; and determine an image of the target volume based on one or more fitted values of the variable intrinsic parameters which match the shape of the fit function to the discrete sequence of transient response signals.

14. The MRI device according to claim 13, comprising a lookup table for distinguishing different tissue types in the image based on one or more distinct fit values of intrinsic parameters depending on tissue type, as fitted to a measured sequence of transient response for a predetermined set of experimental settings.

15. A non-transitory computer readable medium with software instructions which when executed by an MRI device cause the MRI device to:

apply a consecutive series of MRI sequences to a target volume, wherein each MRI sequence comprises an ordered combination of radio frequency excitation pulses and/or magnetic field gradient pulses configured according to experimental settings for manipulating a magnetization state of spin systems to be imaged in the target volume, wherein the MRI sequences are applied during a transient phase with a repetition time between subsequent sequences shorter than a relaxation time of the spin systems to be imaged;

measure a discrete sequence of transient response signals, wherein a respective response signal is acquired during a respective acquisition windows of a respective MRI sequence, wherein the sequence of transient response signals represents sequential evolution of the magnetization state resulting from a combination of the manipulating of the spin systems by the MRI sequences as well as intrinsic properties of the spin systems to be imaged, wherein the transient response signals are measured in respective acquisition windows per MRI sequence during the transient phase before a steady state response signal to the consecutive series of MRI sequences develops;

fit the discrete sequence of transient response signals to a fit function that is based on an analytically modeled evolution of the magnetization state, wherein a shape of the fit function is determined according to the analytically modelled evolution based at least on the experimental settings as well as intrinsic parameters to be fitted, wherein the intrinsic parameters are related to the intrinsic properties of the spin systems to be imaged; and determine an image of the target volume based on one or more fitted values of the variable intrinsic parameters which match the shape of the fit function to the discrete sequence of transient response signals.

16. The non-transitory computer readable medium according to claim 15, further storing a lookup table for distinguishing different tissue types in the image based on one or more distinct fit values of intrinsic parameters depending on tissue type, as fitted to a measured sequence of transient response for a predetermined set of experimental settings.

* * * * *